United States Patent
Petermann et al.

(10) Patent No.: US 10,961,355 B2
(45) Date of Patent: Mar. 30, 2021

(54) AQUEOUS SOLUTION OF CELLULOSE ETHER ACETATE

(71) Applicant: Dow Global Technologies LLC, Midland, MI (US)

(72) Inventors: Oliver Petermann, Hamburg (DE); Jin Zhao, Midland, MI (US)

(73) Assignee: Nutrition & Biosciences USA 1, LLC, Rochester, NY (US)

( * ) Notice: Subject to any disclaimer, the term of this patent is extended or adjusted under 35 U.S.C. 154(b) by 208 days.

(21) Appl. No.: 16/072,673

(22) PCT Filed: May 1, 2017

(86) PCT No.: PCT/US2017/030378
§ 371 (c)(1),
(2) Date: Jul. 25, 2018

(87) PCT Pub. No.: WO2017/205008
PCT Pub. Date: Nov. 30, 2017

(65) Prior Publication Data
US 2019/0119451 A1 Apr. 25, 2019

Related U.S. Application Data
(60) Provisional application No. 62/341,155, filed on May 25, 2016.

(51) Int. Cl.
| | | |
|---|---|---|
| C08J 3/07 | (2006.01) | |
| A61K 9/50 | (2006.01) | |
| A61K 9/48 | (2006.01) | |
| A61K 47/38 | (2006.01) | |
| C08L 1/12 | (2006.01) | |
| A61K 9/28 | (2006.01) | |

(52) U.S. Cl.
CPC ............... *C08J 3/07* (2013.01); *A61K 9/4816* (2013.01); *A61K 9/5042* (2013.01); *A61K 47/38* (2013.01); *C08L 1/12* (2013.01); *A61K 9/2866* (2013.01); *C08J 2301/12* (2013.01); *C08L 2201/54* (2013.01)

(58) Field of Classification Search
CPC . C08L 1/12; C08L 2201/54; C08J 3/07; C08J 2301/12
See application file for complete search history.

(56) References Cited

U.S. PATENT DOCUMENTS

| | | |
|---|---|---|
| 5,776,501 A | 7/1998 | Kokubo et al. |
| 2015/0024054 A1 | 1/2015 | Curatolo et al. |
| 2015/0374831 A1* | 12/2015 | Brackhagen ............ C08B 13/00 424/494 |

FOREIGN PATENT DOCUMENTS

| | | |
|---|---|---|
| WO | 2005115330 | 12/2005 |
| WO | 2014137777 | 9/2014 |
| WO | 2014137778 | 9/2014 |
| WO | 0236637 | 8/2015 |
| WO | 2015126576 | 8/2015 |
| WO | 2015179072 | 11/2015 |

* cited by examiner

*Primary Examiner* — Peter D. Mulcahy

(57) ABSTRACT

An aqueous composition comprising a cellulose ether acetate being at least partially dissolved in an aqueous liquid is produced in a process, wherein an aqueous liquid is mixed with a cellulose ether acetate having a degree of substitution of acetyl groups, DSAc, of from 0.05 to 0.75 and the temperature of the mixture of the cellulose ether acetate and the aqueous liquid is set to less than 10 C to at least partially dissolve the cellulose ether acetate in the aqueous liquid.

10 Claims, No Drawings

AQUEOUS SOLUTION OF CELLULOSE ETHER ACETATE

FIELD

This invention concerns an aqueous composition comprising a cellulose ether acetate, a process for producing it and its use.

INTRODUCTION

International Patent Application WO 2005/115330 discloses hydroxypropyl methyl cellulose acetate (HPMCA) polymers having a degree of substitution of acetyl groups ($DOS_{Ac}$) of from 0.15 to 0.6, preferably from 0.20 to 0.50, and more preferably from 0.25 to 0.45. WO 2005/115330 discloses that low-solubility drugs, particularly hydrophobic drugs, have an increased solubility in HPMCA, as compared to their solubilities in the corresponding hydroxypropyl methyl cellulose (HPMC) from which the HPMCA is produced. HPMCA is useful for increasing the bioavailability of poorly soluble drugs or as controlled-release matrix material. WO 2005/115330 discloses that the HPMCA should be water soluble or dispersible over the physiological pH range of 1-8. However, the reported water-solubilities of at least 0.1 mg/mL, i.e. of at least 0.01 wt.-%, over at least a portion of the pH range of 1 to 8 is extremely low. HPMCA can be dissolved in organic solvents. However, the use of organic solvents often has disadvantages, such as high production costs and potentially remaining amounts of organic solvents in the HPMCA.

In view of the great utility of HPMCA for improving the water solubility of poorly or moderately water-soluble drugs, there is the urgent need to find a way of dissolving cellulose ether acetates, such as HPMCA, in aqueous liquids.

SUMMARY

Surprisingly, an efficient and simple process for least partially dissolving certain cellulose ether acetates in an aqueous liquid has been found.

One aspect of the present invention is a process for producing an aqueous composition comprising a cellulose ether acetate being at least partially dissolved in an aqueous liquid, wherein the process comprises the step of mixing an aqueous liquid with a cellulose ether acetate having a degree of substitution of acetyl groups, $DS_{Ac}$, of from 0.05 to 0.75 and setting the temperature of the mixture of the cellulose ether acetate and the aqueous liquid to less than 10° C. to at least partially dissolve the cellulose ether acetate in the aqueous liquid.

Another aspect of the present invention is a process for manufacturing capsule shells which comprises the steps of producing, according to the above-mentioned process, an aqueous composition comprising a cellulose ether acetate at least partially dissolved in an aqueous liquid, and contacting dipping pins having a higher temperature than the aqueous composition with the aqueous composition or with the portion of the aqueous composition wherein cellulose ether acetate is dissolved.

Yet another aspect of the present invention is a process for coating dosage forms which comprises the steps of producing, according to the above-mentioned process, an aqueous composition comprising a cellulose ether acetate at least partially dissolved in an aqueous liquid, and contacting dosage forms with the aqueous composition or with the portion of the aqueous composition wherein cellulose ether acetate is dissolved.

Yet another aspect of the present invention is a process for preparing a solid dispersion of an active ingredient in a cellulose ether acetate which comprises the steps of producing, according to the above-mentioned process, an aqueous composition comprising a cellulose ether acetate at least partially dissolved in an aqueous liquid, dissolving an active ingredient in the aqueous composition or in the portion of the aqueous composition wherein cellulose ether acetate is dissolved, and drying the aqueous composition or the portion of the aqueous composition wherein cellulose ether acetate and active ingredient are dissolved to produce the solid dispersion of an active ingredient in a hydroxyalkyl methylcellulose acetate.

Yet another aspect of the present invention is an aqueous composition which comprises at least 2.0 weight percent of a cellulose ether acetate dissolved in an aqueous liquid, wherein the cellulose ether acetate has a degree of substitution of acetyl groups, $DS_{Ac}$, of from 0.05 to 0.75 and the aqueous composition is producible by the above-mentioned process.

Yet another aspect of the present invention is an aqueous composition which comprises at least 2.0 weight percent of a cellulose ether acetate dissolved in an aqueous liquid, wherein the cellulose ether acetate has a degree of substitution of acetyl groups, $DS_{Ac}$, of from 0.05 to 0.75 and the aqueous composition has a temperature of no more than 10° C.

Yet another aspect of the present invention is coated dosage form wherein the coating comprises at least one cellulose ether acetate having a degree of substitution of acetyl groups, $DS_{Ac}$, of from 0.05 to 0.75.

Yet another aspect of the present invention is a polymeric capsule shell which comprises at least one cellulose ether acetate having a degree of substitution of acetyl groups, $DS_{Ac}$, of from 0.05 to 0.75.

Yet another aspect of the present invention is a capsule which comprises an above-mentioned capsule shell and further comprising a drug or a nutritional or food supplement or a combination thereof.

DESCRIPTION OF EMBODIMENTS

Surprisingly, it has been found that a cellulose ether acetate, such as hydroxypropyl methylcellulose acetate (HPMCA), is at least partially dissolved in an aqueous liquid when a) the cellulose ether acetate has a degree of substitution of acetyl groups, $DS_{Ac}$, of from 0.05 to 0.75 and b) the temperature of the mixture of the cellulose ether acetate and the aqueous liquid is set to less than 10° C., preferably to less than 8° C., more to preferably less than 5° C., and particularly to 3° C. or less. At least 2.0 wt.-% cellulose ether acetate solutions in water can be produced. When the degree of substitution of acetyl groups, $DS_{Ac}$, is higher than 0.75, the cellulose ether acetate is not soluble in the aqueous liquid, even not at a temperature of less than 10° C.

When the temperature of the mixture has a higher temperature, such as room temperature, 2.0 wt.-% cellulose ether acetate solutions in water can only be prepared when the cellulose ether acetate has a $DS_{Ac}$ of less than 0.20. The observed dissolution of cellulose ether acetate, such as HPMCA, in water at room temperature is surprising in view of the teaching of International Patent Application No. WO 2005/115330, which discloses a water-solubility of only 0.1 mg/mL or more, i.e. of 0.01 wt. % or more. Unfortunately, such a low $DS_{Ac}$ of the cellulose ether acetate, such as HPMCA, is not desired in some end-uses. A $DS_{Ac}$ of less than 0.20 is also below the preferred $DS_{Ac}$ range for HPMCA in International Patent Application No. WO 2005/115330.

The cellulose ether acetate used in the process of the present invention has a cellulose backbone having β-1,4 glycosidically bound D-glucopyranose repeating units, designated as anhydroglucose units in the context of this invention. The cellulose ether acetate preferably is an alkyl cellulose acetate, hydroxyalkyl cellulose acetate or hydroxyalkyl alkylcellulose acetate. This means that in the cellulose ether acetate at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the cellulose ether acetate. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined cellulose ether acetates are alkylcellulose acetates, such as methylcellulose acetates and propylcellulose acetates; hydroxyalkylcellulose acetates, such as hydroxyethylcellulose acetates, hydroxypropylcellulose acetates, and hydroxybutylcellulose acetates; and hydroxyalkyl alkylcellulose acetates, such as hydroxyethyl methylcellulose acetates, hydroxymethyl ethylcellulose acetates, ethyl hydroxyethylcellulose acetates, hydroxypropyl methylcellulose acetates, hydroxypropyl ethylcellulose acetates, hydroxybutyl methylcellulose acetates, and hydroxybutyl ethylcellulose acetates; and those having two or more hydroxyalkyl groups, such as hydroxyethylhydroxypropyl methylcellulose acetates. Most preferably, the cellulose ether acetate is a hydroxyalkyl methylcellulose acetate, such as a hydroxypropyl methylcellulose acetate (HPMCA).

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the cellulose ether acetate. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The cellulose ether acetate generally has a molar substitution of hydroxyalkoxyl groups in the range 0.05 to 1.00, preferably 0.08 to 0.70, more preferably 0.15 to 0.60, most preferably 0.15 to 0.40, and particularly 0.20 to 0.40.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The cellulose ether acetates generally have a DS(alkoxyl) in the range of 1.0 to 2.5, preferably from 1.2 to 2.2, more preferably from 1.6 to 2.05, and most preferably from 1.7 to 2.05.

Most preferably, the cellulose ether acetate is a hydroxyalkyl methylcellulose acetate, such as a hydroxypropyl methylcellulose acetate (HPMCA) having a DS(methoxyl) within the ranges indicated above for DS(alkoxyl) and an MS(hydroxypropoxyl) within the ranges indicated above for MS(hydroxyalkoxyl).

The cellulose ether acetate comprises acetyl groups as the only ester groups; i.e., the cellulose ether acetate utilized in the present invention does not comprise any ester groups different from acetyl. The cellulose ether acetate has a degree of substitution of acetyl groups, $DS_{Ac}$, of at least 0.05, generally at least 0.10, preferably at least 0.20, more preferably at least 0.25, most preferably at least 0.30 and in some embodiments of the invention even at least 0.40 or even at least 0.45. Although it has surprisingly been found that 2.0 wt.-% cellulose ether acetate solutions in water can even be prepared at room temperature if the cellulose ether acetate has a $DS_{Ac}$ of less than 0.20, nevertheless preferred cellulose ether acetates have a $DS_{Ac}$ at least 0.20, more preferably at least 0.25, most preferably at least 0.30 and in some embodiments of the invention even at least 0.40 or even at least 0.45. Such preferred cellulose ether acetates have been found to gel at elevated temperatures as described in the Examples section, depending on their concentration in water. The HPMCA has a degree of substitution of acetyl groups of up to 0.75, preferably up to 0.70, more preferably up to 0.69 and in some embodiments up to 0.67.

The ester substitution with acetyl groups (—CO—CH$_3$) is determined as described for Hypromellose Acetate Succinate, United States Pharmacopia and National Formulary, NF 29, pp. 1548-1550", except that stirring in 1.0 N NaOH is conducted for 12 hours instead of for 4 hours. Reported values for ester substitution are corrected for volatiles (determined as described in section "loss on drying" in the above HPMCAS monograph).

The content of ether groups in the cellulose ether acetate is determined in the same manner as described for "Hypromellose", United States Pharmacopeia and National Formulary, USP 35, pp 3467-3469.

The contents of ether and acetate groups obtained by the above analyses are converted to DS and MS values of individual substituents according to the formulas below. The formulas may be used in analogue manner to determine the DS and MS of substituents of other cellulose ether esters.

% cellulose backbone $$\% \text{ cellulose backbone} = 100 - \left(\% \text{ MeO} * \frac{M(OCH_3) - M(OH)}{M(OCH_3)}\right) -$$

$$\left(\% \ HPO * \frac{M(OCH_2CH(OH)CH_3) - M(OH)}{M(OCH_2CH(OH)CH_3)}\right) -$$

$$\left(\% \ Acetyl * \frac{M(COCH_3) - M(H)}{M(COCH_3)}\right)$$

$$DS(Me) = \frac{\frac{\% \ MeO}{M(OCH_3)}}{\frac{\% \ cellulose \ backbone}{M(AGU)}}$$

$$MS(HP) = \frac{\frac{\% \ HPO}{M(HPO)}}{\frac{\% \ cellulose \ backbone}{M(AGU)}}$$

$$DS(Acetyl) = \frac{\frac{\% \ Acetyl}{M(Acetyl)}}{\frac{\% \ cellulose \ backbone}{M(AGU)}}$$

$M(MeO) = M(OCH_3) = 31.03 \ Da$ $M(Acetyl) = M(COCH_3) = 43.04 \ Da$ $M(AGU) = 162.14 \ Da$ $M(OH) = 17.008 \ Da$ $M(HPO) = M(OCH_2CH(OH)CH_3) = 75.09 \ Da$ $M(H) = 1.008 \ Da$ By convention, the weight percent is an average weight percentage based on the total weight of the cellulose repeat unit, including all substituents. The content of the methoxyl group is reported based on the mass of the methoxyl group (i.e., —$OCH_3$). The content of the hydroxyalkoxyl group is reported based on the mass of the hydroxyalkoxyl group (i.e., —O— alkylene-OH); such as hydroxypropoxyl (i.e., —O—$CH_2CH(CH_3)$—OH). The content of the acetyl groups is reported based on the mass of acetyl (—C(O)—$CH_3$).

The cellulose ether acetate utilized in the present invention generally has a viscosity of up to 200 mPa·s, preferably up to 100 mPa·s, more preferably up to 50 mPa·s, and most preferably up to 5.0 mPa·s, measured as a 2.0 wt.-% solution of the cellulose ether acetate in 0.43 wt.-% aqueous NaOH at 20° C. Generally the viscosity is at least 1.2 mPa·s, more typically at least 1.8 mPa·s, even more typically at least 2.4 mPa·s, and most typically at least 2.8 mPa·s, measured as a 2.0 wt.-% solution of the cellulose ether acetate in 0.43 wt.-% aqueous NaOH at 20° C.

The cellulose ether acetate utilized in the present invention generally has a weight average molecular weight $M_w$ of up to 500,000 Dalton, preferably up to 200,000 Dalton, more preferably up to 150,000 Dalton, and most preferably up to 100,000 Dalton or up to 50,000 Dalton. Generally it has a weight average molecular weight $M_w$ of at least 10,000 Dalton, preferably at least 15,000 Dalton, more preferably at least 20,000 Dalton. The cellulose ether acetate generally has a Polydispersity $M_w/M_n$, i.e., a ratio of weight average molecular weight $M_w$ to number average molecular weight $M_n$, of at least 1.2, typically at least 1.3. Moreover, the cellulose ether acetate generally has a Polydispersity of up to 2.6, preferably of up to 2.3, more preferably of up to 1.9, and most preferably up to 1.6. $M_w$ and $M_n$ are measured according to Journal of Pharmaceutical and Biomedical Analysis 56 (2011) 743 using a mixture of 40 parts by volume of acetonitrile and 60 parts by volume of aqueous buffer containing 50 mM $NaH_2PO_4$ and 0.1 M $NaNO_3$ as mobile phase. The mobile phase is adjusted to a pH of 8.0.

The temperature of the aqueous liquid with which the above described cellulose ether acetate is mixed preferably is 0° C. or more, typically 0.5° C. or more. The temperature of the aqueous liquid is typically up to 20° C., preferably less than 10° C., more preferably less than 8° C., even more preferably less than 5° C., and most preferably up to 3° C. Generally the cellulose ether acetate is blended with at least 5 weight parts, preferably at least 10 weight parts, more preferably at least 20 weight parts, and generally up to 100 weight parts, preferably up to 60 weight parts, more preferably up to 40 weight parts, of aqueous liquid per weight part of cellulose ether acetate.

It is essential in the process of the present invention that the temperature of the resulting mixture of the cellulose ether acetate and the aqueous liquid is set to less than 10° C., preferably less than 8° C., more preferably less than 5° C., and most preferably to 3° C. or less. The temperature of the resulting mixture is generally set to at least minus 2° C., typically to 0° C. or more, and more typically to 0.5° C. or more. It is not essential whether the temperature of the aqueous liquid is adjusted before or after mixing with the cellulose ether acetate. Preferably the mixture is kept at the above-mentioned temperature for a time period of at least 10 minutes, preferably at least 30 minutes, and more preferably at least 2 hours. Depending on the type of cellulose ether acetate, the dissolution process in the aqueous liquid can take quite a long time. Generally the mixture of the cellulose ether acetate and the aqueous liquid is kept at the above-mentioned temperature for a time period of up to a week, preferably up to 72 hours, and more preferably up to 24 hours.

The aqueous liquid may additionally comprise a minor amount of an organic liquid diluent; however, the aqueous liquid should generally comprise at least 80, preferably at least 85, more preferably at least at least 90, and particularly at least 95 weight percent of water, based on the total weight of the aqueous liquid. The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. Most preferably, the aqueous liquid comprises from 80 to 100 percent, preferably 85 to 100 percent, more preferably 90 to 100 percent and most preferably 95 to 100 percent of water, and from 0 to 20 percent, preferably 0 to 15 percent, more preferably 0 to 10 percent, and most preferably 0 to 5 percent of an organic liquid diluent, based on the total weight of the aqueous liquid. Most preferably the aqueous liquid consists of water, e.g., deionized or distilled water.

Surprisingly, at least a portion of the above-described cellulose ether acetate can be dissolved in the aqueous liquid described above under the above-mentioned temperature conditions, i.e., at a temperature of less than 10° C., preferably less than 8° C., more preferably less than 5° C., and most preferably at 3° C. or less. Generally at least 2.0 wt.-%, typically at least 5.0 wt.-%, more typically at least 10 wt.-%, and in some cases even at least 15 wt.-% cellulose ether acetate can be dissolved in the aqueous liquid at such temperature. Generally up to 20 wt.-%, or in preferred embodiments even up to 30 wt.-%, of cellulose ether acetate can be dissolved in the aqueous liquid at such temperature. The percentages are based on the total weight of cellulose ether acetate and aqueous liquid. After complete or partial dissolution of the cellulose ether acetate in the aqueous liquid, the temperature of the aqueous composition comprising dissolved cellulose ether acetate can be slightly increased, e.g., to a temperature of not more than 25° C., typically not more than 20° C., without precipitation of the dissolved cellulose ether acetate. Only upon further temperature increase dissolved cellulose ether acetate starts to gel. Aqueous cellulose ether acetate solutions of the present invention gel at elevated temperature, typically at 25 to 70° C., more typically at 30 to 60° C., depending on the concentration of the cellulose ether acetate in water and on the $DS_{Ac}$ of the cellulose ether acetate. This temperature-dependent gelation capability of cellulose ether acetate that is dissolved in an aqueous liquid makes the aqueous composition comprising dissolved cellulose ether acetate highly useful for preparing capsule shells.

Another aspect of the present invention is an aqueous composition which comprises at least 2.0 weight percent of a cellulose ether acetate dissolved in an aqueous liquid, wherein the cellulose ether acetate has a degree of substitution of acetyl groups, $DS_{Ac}$, of from 0.05 to 0.75 and the aqueous composition has a temperature of no more than 10° C. Preferred cellulose ether acetates and preferred aqueous liquids are described further above. The temperature of the aqueous composition preferably is less than 10° C., more preferably less than 8° C., even more preferably less than 5° C., and most preferably 3° C. or less. The temperature of the aqueous composition is generally at least minus 2° C., typically at least 0° C., and more typically at least 0.5° C. The aqueous composition typically comprises at least 3.0 wt.-%, preferably at least 5.0 wt.-%, more preferably at least 10 wt.-%, and in some cases even at least 15 wt.-% cellulose ether acetate dissolved in the aqueous liquid. Aqueous compositions comprising up to 20 wt.-%, or in preferred embodiments even up to 30 wt.-%, of cellulose ether acetate dissolved in the aqueous liquid can generally be prepared at the above-mentioned temperatures. The term "x wt.-% cellulose ether acetate dissolved in the aqueous liquid" as used herein means that x g of the cellulose ether acetate is dissolved in (100−x) g of the aqueous liquid, such as water. The composition may comprise one or more active ingredients, such as fertilizers, herbicides or pesticides, or biologically active ingredients, such as vitamins, herbals and mineral supplements or drugs. The term "drug" is conventional, denoting a compound having beneficial prophylactic and/or therapeutic properties when administered to an animal, especially humans. The aqueous composition may further comprise optional additives, such as coloring agents, pigments, opacifiers, flavor and taste improvers, antioxidants, and any combination thereof. Optional additives are preferably pharmaceutically acceptable.

Another aspect of the present invention is a process for manufacturing capsule shells wherein an aqueous composition comprising a cellulose ether acetate at least partially dissolved in an aqueous liquid is produced as described above and dipping pins are contacted with the aqueous composition or with the portion of the aqueous composition wherein cellulose ether acetate is dissolved. The dipping pins should have a higher temperature than the aqueous composition. The aqueous composition which has been prepared at a temperature of less than 10° C. as described above can be contacted directly with dipping pins. Alternatively, the aqueous composition comprising dissolved cellulose ether acetate can be allowed to warm up, e.g., to a temperature of not more than 25° C., typically not more than 20° C., without gelation of the dissolved cellulose ether acetate before it is contacted with dipping pins. Typically the dipping pins have a temperature of at least 30° C., preferably at least 40° C., more preferably at least 45° C., and up to 95° C., preferably up to 70° C., and more preferably up to 60° C. When the cellulose ether acetate is completely or nearly completely dissolved in the aqueous liquid according to the process of the present invention, the dipping pins are contacted with the aqueous composition which comprises the cellulose ether acetate dissolved in the aqueous liquid. When the cellulose ether acetate is only partially dissolved in the aqueous liquid according to the process of the present invention, the dipping pins are contacted with the portion of the aqueous composition wherein cellulose ether acetate is dissolved. In one embodiment the non-dissolved portion of the cellulose ether acetate is separated from the portion of the aqueous composition wherein cellulose ether acetate is dissolved before the aqueous composition is contacted with the dipping pins. In a preferred embodiment the non-dissolved portion of the cellulose ether acetate is not separated but left as sediment in the aqueous composition. The dipping pins can simply be dipped into the supernatant liquid portion of the aqueous composition wherein cellulose ether acetate is dissolved. The procedure allows a very efficient process for producing capsules from aqueous compositions wherein cellulose ether acetates are only partially dissolved.

Another aspect of the present invention is a process for coating dosage forms, such as tablets, granules, pellets, caplets, lozenges, suppositories, pessaries or implantable dosage forms, wherein an aqueous composition comprising an cellulose ether acetate at least partially dissolved in an aqueous liquid is produced as described above and dosage forms are contacted with the aqueous composition or with the portion of the aqueous composition wherein cellulose ether acetate is dissolved. When the cellulose ether acetate is only partially dissolved in the aqueous liquid according to the process of the present invention, the dosage forms are contacted with the portion of the aqueous composition wherein cellulose ether acetate is dissolved, e.g., by spraying this portion of the aqueous composition onto the dosage forms.

Another aspect of the present invention is a coated dosage form wherein the coating comprises at least one cellulose ether acetate having a degree of substitution of acetyl groups, $DS_{Ac}$, of from 0.05 to 0.75. Yet another aspect of the present invention is a polymeric capsule shell which comprises at least one cellulose ether acetate having a degree of substitution of acetyl groups, $DS_{Ac}$, of from 0.05 to 0.75. Yet another aspect of the present invention is a capsule which comprises an above-mentioned capsule shell and further comprising a drug or a nutritional or food supplement or a combination thereof. Preferred cellulose ether acetates for use in coatings or capsule shells and preferred types of dosage forms are described above. The amount of the cellulose ether acetate in the capsule shell or the coating of the dosage form typically is at least 60 percent, more typically at least 70 percent, and most typically at least 80 percent, based on the total weight of the coatings or capsule shell. The amount of the cellulose ether acetate in the capsule shell or the coating of the dosage form can be up to 100 percent, but typically it is up to 95 percent or up to 90 percent, based on the total weight of the coatings or capsule shell.

Films prepared from the aqueous composition of the present invention, such as capsules ore coatings, do not disintegrate in the liquids present in the human stomach, the intestine or colon. Such films, e.g., capsules ore coatings, can be used in the pharmaceutical art for diffusion controlled release of active ingredients, such as drugs, through the cellulose ether acetate film. Hence, the present invention provides unique controlled release capsules or coatings from aqueous cellulose ether acetate solutions. The diffusion of the active ingredient through the cellulose ether acetate film can be controlled by the thickness of the film or by the inclusion of one or more plasticizers which can act as pore formers in the aqueous composition of the present invention. Typical water-soluble plasticizers are monomeric compounds or polymeric compounds having a weight average molecular weight of up to 10,000, preferably triethyl citrate, triacetin, polyethylene glycol, particularly polyethylene glycol having a weight average molecular weight of 2000 to 6000, such as PEG 4000, a polyethylene sorbitan monooleate, commercially available under the Trademark Tween, such as Tween 20 or Tween, 80. The amount of the plasticizer typically is up to 50 percent, preferably up to 40 percent, more preferably up to 30 percent, and most preferably only up to 25 percent, based on the weight of the cellulose ether acetate. The amount of the plasticizer, if any, typically is at least 2 percent, more typically at least 5 percent, and most typically at least 10 percent, based on the weight of the cellulose ether acetate. Alternatively, diffusion of the active ingredient through the cellulose ether acetate film can be controlled by one or more passageway through the cellulose ether acetate film, such as one or more apertures, bores, holes, weaken areas or erodible elements, such as one or more drilled passageways.

Films prepared from the aqueous composition of the present invention, such as capsules or coatings, may comprise optional adjuvants, such as one or more gelling agents, coloring agents, pigments, opacifiers, flavor and taste improvers, antioxidants, and any combination thereof. Optional additives are preferably pharmaceutically acceptable. The amount of the optional additives is typically up 40 percent, more typically up to 20 percent, and most typically up to 10 percent, based on the total weight of the capsule shell.

Another aspect of the present invention is a process for preparing a solid dispersion of an active ingredient, such as a drug, in a cellulose ether acetate wherein an aqueous composition comprising a cellulose ether acetate at least partially dissolved in an aqueous liquid is produced as described above and an active ingredient is dissolved in the aqueous composition or in the portion of the aqueous composition wherein cellulose ether acetate is dissolved, and the resulting aqueous composition, or the resulting portion of the aqueous composition wherein cellulose ether acetate and active ingredient are dissolved, is dried to produce the solid dispersion of an active ingredient in a cellulose ether acetate. A preferred drying method is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Frog. Monogr. Series 2 (1954), and Masters, Spray Drying Handbook (Fourth Edition 1985). A useful spray-drying process is described in the International Patent Application WO 2005/115330, page 34, line 7-page 35, line 25.

Some embodiments of the invention will now be described in detail in the following Examples. Unless otherwise mentioned, all parts and percentages are by weight. In the Examples the following test procedures are used.

EXAMPLES

Content of Ether and Ester Groups

The content of ether groups in the hydroxypropyl methylcellulose acetate (HPMCA) is determined in the same manner as described for "Hypromellose", United States Pharmacopeia and National Formulary, USP 35, pp 3467-3469.

The ester substitution with acetyl groups ($-CO-CH_3$) is determined as described for Hypromellose Acetate Succinate, United States Pharmacopia and National Formulary, NF 29, pp. 1548-1550", except that stirring in 1.0 N NaOH is conducted for 12 hours instead of for 4 hours. Reported values for ester substitution are corrected for volatiles (determined as described in section "loss on drying" in the above HPMCAS monograph).

Water-Solubility at 2° C.

2.5 weight parts of HPMCA, based on its dry weight, were added to 97.5 weight parts of deionized water having a temperature of 2° C. followed by stirring for 6 hours at 2° C. and storing for 16 h at 2° C.

A weighed amount of the mixture was transferred to a weighed centrifuge vial; the transferred weight of the mixture was noted as M1 in g. The transferred weight of HPMCA [M2] was calculated as (transferred weight of mixture in g/100 g×2.5 g). The mixture was centrifuged for 60 min at 5000 rpm (2823×g, Biofuge Stratos centrifuge from Thermo Scientific) at 2° C. After centrifugation an aliquot was removed from the liquid phase and transferred to a dried weighed vial. The weight of the transferred aliquot was recorded as M3 in g. The aliquot was dried at 105° C. for 12 h. The remaining g of HPMCA was weighted after drying and recorded as M4 in g.

The term "% water–soluble (conc.=2.5%, T=2° C.) expresses the percentage of HPMCA that is actually dissolved in the mixture of 2.5 weight parts of HPMCA and 97.5 weight parts of deionized water having a temperature of 2° C. It is calculated as (M4/M2)×(M1/M3)×100, which corresponds to (g HPMCA in liquid aliquot/g HPMCA transferred to centrifuge vial)×(g mixture transferred to centrifuge vial/g liquid aliquot after centrifugation)×100. In the formulas above "x" stands for the multiplication operator.

Water-Solubility at 21° C.

For comparative purposes, 2.5 weight parts of HPMCA, based on its dry weight, were added to 97.5 weight parts of deionized water having room temperature (21° C.), followed by stirring for 6 hours at room temperature and storing for 16 h at room temperature. The determination of the % water solubility at 2.5% at 21° C. was carried out as described above expect that the mixture was centrifuged at 21° C. The term "% water–soluble (conc.=2.5%, T=21° C.) expresses the percentage of HPMCA that is actually dissolved in the mixture of 2.5 weight parts of HPMCA and 97.5 weight parts of deionized water having a temperature of 21° C.

Viscosity of Hydroxypropyl Methyl Cellulose Acetate (HPMCA)

The 2.0% by weight solution of the HPMCA in 0.43 wt. % aqueous NaOH was prepared as described in "Hypromellose Acetate Succinate, United States Pharmacopia and National Formulary, NF 29, pp. 1548-1550" An Ubbelohde viscosity measurement according to DIN 51562-1:1999-01 (January 1999) was carried out. The measurement was done at 20° C. The 2.0% by weight solution of the HPMCA in 0.43 wt. % aqueous NaOH is listed in Table 2 below as "2.0% viscosity in 0.43% NaOH".

Gelation Temperature and Gel Strength of Solutions of HPMCA in Water

A 2 wt.-%, 5 wt.-% or 10 wt.-% solution of HPMCA in water was produced by adding a corresponding amount of milled, ground, and dried HPMCA (under consideration of the water content of the HPMCA) to water (temperature 20-25° C.) at room temperature while stirring with an overhead lab stirrer at 750 rpm with a 3-wing (wing=2 cm) blade stirrer. The solution was then cooled to about 1.5° C. After the temperature of 1.5° C. was reached the solution was stirred for 120 min at 500 rpms. Each solution was stored in the refrigerator prior to the characterization.

Rheology measurements of the HPMCA solutions in water were conducted with a Haake RS600 (Thermo Fisher Scientific) rheometer with cup and bob fixtures (CC-25). The samples were heated at a rate of 1° C. per minute over a temperature range from 5 to 85° C. with a constant strain (deformation) of 2% and a constant angular frequency of 2 Hz. The measurement collection rate was chosen to be 4 data points/min. The storage modulus G', which was obtained from the rheology measurements, represents the elastic properties of the solution and represents the gel strength in the high temperature region, when the storage modulus G' is higher than the loss modulus G".

The obtained data of the storage modulus G', which was obtained from the oscillation measurements, was first logarithmized and normalized to G' (min) to zero and G' (max) to 100. Linear regression curves were fitted to subsets of these storage modulus data (increments of 5 data points). A tangent was fitted to the steepest slope of the regression curve. The intersection of this tangent with the x-axis is reported as gelation temperature. Details how to determine the gelation temperature are described in International Patent Application WO2015/009796 on pages 18 and 19 in the paragraphs "Determination of the gelation temperature of aqueous compositions comprising methyl cellulose".

The gel strength according to the storage modulus G' at 70° C. was also obtained by this rheology measurement.

Production of HPMCA of Comparative Example A and Examples 1-11

700.0 g of acetic acid was filled in a reactor and stirred. Then 230.0 g of sodium acetate (water free) and 230.0 g of HPMC (water free) were added. The HPMC had a methoxyl substitution ($DS_M$) of 1.96, a hydroxypropoxyl substitution ($MS_{HP}$) of 0.25 and a viscosity of 3.0 mPa·s, measured as a 2% solution in water at 20° C. according to ASTM D2363-79 (Reapproved 2006). The weight average molecular weight of the HPMC was about 20,000 Dalton. The HPMC is commercially available from The Dow Chemical Company as Methocel E3 LV Premium cellulose ether. Inertisation with nitrogen was carried out. The mixture was heated to 85° C. under stirring. After reaching the temperature of 85° C. the reaction mixture was allowed to stir for 10 min. Then acetic anhydride as listed in Table 1 below was added, and the reaction mixture was allowed to react for 4 hours. After the esterification reaction the mixture was quenched with 19.4 g of deionized water having a temperature of 50° C. Then 2 L of deionized water (temperature 50° C.) was added into the reactor under stirring to precipitate the HPMCA. The precipitated HPMCA cooled down to about 50° C. and was removed from the reactor. The HPMCA was washed twice with 1.7 L of hot water (temperature about 95°) by applying high shear mixing using an Ultra-Turrax stirrer S50-G45 running at 5000 rpm for 60 seconds. After filtration the filter cake was washed several times with 1.7 L of hot water. The washed HPMCA was isolated by vacuum-filtration and dried at 55° C. overnight.

TABLE 1

| (Comp.) Example | HPMC | | Glacial acetic acid | | Acetic anhydride | | Sodium acetate | |
|---|---|---|---|---|---|---|---|---|
| | g | Mol | g | mol/mol HPMC | g | mol/mol HPMC | g | mol/mol HPMC |
| A | 230 | 1.14 | 700 | 10.3 | 200 | 1.80 | 230 | 2.46 |
| 1 | 230 | 1.14 | 700 | 10.3 | 130 | 1.17 | 230 | 2.46 |
| 2 | 230 | 1.14 | 700 | 10.3 | 100 | 0.90 | 230 | 2.46 |
| 3 | 230 | 1.14 | 700 | 10.3 | 80 | 0.72 | 230 | 2.46 |
| 4 | 230 | 1.14 | 700 | 10.3 | 50 | 0.45 | 230 | 2.46 |
| 5 | 230 | 1.14 | 700 | 10.3 | 40 | 0.36 | 230 | 2.46 |
| 6 | 230 | 1.14 | 700 | 10.3 | 30 | 0.27 | 230 | 2.46 |
| 7 | 230 | 1.14 | 700 | 10.3 | 110 | 0.99 | 230 | 2.46 |
| 8 | 230 | 1.14 | 700 | 10.3 | 120 | 1.08 | 230 | 2.46 |
| 9 | 230 | 1.14 | 700 | 10.3 | 130 | 1.17 | 230 | 2.46 |
| 10 | 230 | 1.14 | 700 | 10.3 | 140 | 1.28 | 230 | 2.46 |
| 11 | 230 | 1.14 | 700 | 10.3 | 150 | 1.35 | 230 | 2.46 |

The properties of the HPMCA of Examples 1-11 and Comparative Example A are listed in Table 2 below. In Table 2 the abbreviations have the following meanings:

$DS_M$=DS(methoxyl): degree of substitution of methoxyl groups;

$MS_{HP}$=MS(hydroxypropoxyl): molar substitution of hydroxypropoxyl groups;

$DS_{Ac}$: degree of substitution of acetyl groups.

TABLE 2

| (Comparative) Example | Methoxyl (%) | Hydroxy-propoxyl (%) | acetyl (%) | $DS_{Ac}$ | % water-soluble (conc. = 2.5%, T = 2° C.) | % water-soluble (conc. = 2.5%, T = 21° C.) | 2% viscosity in 0.43% NaOH [mPa · s] |
|---|---|---|---|---|---|---|---|
| A | 25.4 | 8.0 | 14.7 | 0.82 | 74 | 2 | not dissolved |
| 1 | 25.7 | 8.3 | 12.1 | 0.65 | 86 | 22 | 3.7 |
| 2 | 26.3 | 8.2 | 9.4 | 0.49 | 98 | 31 | 3.8 |
| 3 | 27.7 | 8.6 | 6.7 | 0.34 | 98 | 68 | 3.6 |

TABLE 2-continued

| (Comparative) Example | Methoxyl (%) | Hydroxy-propoxyl (%) | acetyl (%) | $DS_{Ac}$ | % water-soluble (conc. = 2.5%, T = 2° C.) | % water-soluble (conc. = 2.5%, T = 21° C.) | 2% viscosity in 0.43% NaOH [mPa · s] |
|---|---|---|---|---|---|---|---|
| 4 | 28.6 | 8.7 | 3.8 | 0.19 | 98 | 99 | 3.7 |
| 5 | 29.0 | 8.8 | 3.2 | 0.16 | 99 | 100 | 4.2 |
| 6 | 29.4 | 8.8 | 2.5 | 0.12 | 99 | 98 | 4.1 |
| 7 | 26.4 | 8.3 | 10.4 | 0.55 | 100 | 41 | 3.1 |
| 8 | 26.4 | 8.4 | 11.1 | 0.60 | 100 | 38 | 3.1 |
| 9 | 26.1 | 8.2 | 11.9 | 0.64 | 94 | 31 | 3.0 |
| 10 | 25.9 | 8.1 | 12.3 | 0.67 | 86 | 25 | 3.0 |
| 11 | 25.9 | 8.1 | 12.5 | 0.68 | 87 | 19 | Not dissolved |

The results in Table 2 above illustrate that by the process of the present invention cellulose ether acetate, such as HPMCA having a degree of substitution of acetyl groups, $DS_{Ac}$, of up to 0.75 can be brought into solution by setting the temperature of the mixture of the cellulose ether acetate and the aqueous liquid to less than 10° C. When trying to dissolve the HPMCA at room temperature as done in the prior art, no sufficient solubility is achieved, except in Examples 3-5 which have a $DS_{Ac}$ of only 0.19, 0.16 and 0.12, respectively. This is below the $DOS_{Ac}$ that is taught to be preferred in International Patent Application No. WO 2005/115330.

Warming Up of Aqueous HPMCA Solutions

The aqueous HPMCA solutions of the present invention were by mixing 2.0 weight parts of HPMCA and 98.0 weight parts of water under vigorous stirring in an ice bath. The produced mixtures were then visually inspected. Subsequently the mixtures were gradually warmed up by first storing them in a refrigerator, then at room temperature for 1 hour, then at 40° C. for 1 hour, then at 50° C. for 1 hour, and then at 60° C. for 1 hour. The effect of the temperature increase on the solutions was visually inspected.

It is surprising that the HPMCA samples gel in spite of their low degree of substitution of acetyl groups. The HPMC that is used as starting material for preparing the HPMCA does not gel at a concentration of 2.0 wt.-%. A 2.0 wt.-% solution of Methocel E3 LV Premium cellulose ether in water after heating to 70° C. does not form a gel but only flocculates.

Rheology measurements were carried out to measure the gelation temperatures and gel strength according to the storage modulus G' at 70° C. of 2.0 wt.-%, 5.0 wt.-% and 10.0 wt.-% solutions of the HPMCA of Examples 1-6 in water as described further above. The results are listed in Table 4 below.

TABLE 4

| Example | Wt.-% HPMCA in water | Gelation Temperature, ° C. | Gel Strength G' at 70° C., Pa |
|---|---|---|---|
| 1 | 2.0 | 39 | 31 |
| 1 | 5.0 | 29 | 1550 |
| 1 | 10.0 | 26 | 8400 |
| 2 | 2.0 | 37 | 266 |

TABLE 3

| (Comp.) Example | After 6 hours in ice bath | After 12 h in refrigerator | After 1 h at room temperature | After 1 hour at 40° C. | After 1 hour at 50° C. | After 1 hour at 60° C. |
|---|---|---|---|---|---|---|
| A | Turbid, many flakes | Turbid, slimy sediment | Turbid, slimy sediment | Milky, sediment | Milky, flocky gel | Not assessed |
| 1 | Turbid, dissolved | Slightly turbid, dissolved | Turbid solution | Milky, gel-type, flocky | Milky, flocky gel | Not assessed |
| 2 | Nearly dissolved | Clear solution | Nearly clear sol., fibrous flakes | Milky, stable gel[1] | White, stable gel[1] | Not assessed |
| 3 | Clear solution | Clear solution | Clear solution | Opal solution | White, instable gel | Not assessed |
| 4 | Clear solution | Clear solution | Clear solution | Slightly opal solution | Opal solution, slight gelling | Not assessed |
| 5 | Clear solution | Clear solution | Clear solution | Clear solution | Opal solution, slight gelling | Not assessed |
| 6 | Clear solution | Clear solution | Clear solution | Clear solution | Opal solution, very slight gelling | Not assessed |
| 7 | not assessed | Slightly turbid, dissolved | Not assessed | Milky, soft gel | Milky, instable white gel | Milky, white gel[1] |
| 8 | not assessed | Somewhat turbid, dissolved | Not assessed | Milky, soft gel | Milky, white gel[1] | Milky, white gel[1] |
| 9 | not assessed | Turbid, dissolved | Not assessed | Milky, soft gel | Milky, white gel[1] | Milky, white gel[1] |
| 10 | not assessed | Turbid, dissolved, some flakes | Not assessed | Milky, soft gel | Milky, white gel[1] | Milky, white gel[1] |
| 11 | not assessed | Turbid, dissolved | Not assessed | Milky, soft gel | Milky, white gel[1] | Milky, white gel[1] |

[1] gel in container does not flow when container is turned upside down

Gelation

Aqueous HPMCA solutions of the present invention gel at elevated temperature, typically at 25 to 70° C., more typically at 30 to 60° C., depending on the concentration of the HPMCA in water and on the $DS_{Ac}$ of the HPMCA. Typically the HPMCA even gel at a concentration as low as 2.0 wt.-%.

TABLE 4-continued

| Example | Wt.-% HPMCA in water | Gelation Temperature, ° C. | Gel Strength G' at 70° C., Pa |
|---|---|---|---|
| 2 | 5.0 | 24 | 5260 |
| 3 | 2.0 | 44 | 250 |
| 4 | 2.0 | 52 | 158 |
| 5 | 2.0 | 54 | 116 |
| 6 | 2.0 | 56 | 89 |
| Methocel E3 LV | 2.0 | 55 | 1.1* |
| Premium cellulose ether | 5.0 | 63 | 13 |
| | 10.0 | 58 | 385 |

*No significant gelling, only flocculation

Preparation of Capsules from HPMCA of Examples 1 and 2

An aqueous solution of 8.5 wt.-% of the HPMCA of Example 1 or 2 was prepared by dissolving the HPMCA in deionized water at a temperature of 4° C. Then 22 wt.-% of triethyl citrate (TEC), based on the weight of HPMCA, was added to the aqueous solution at 4° C. and the solution was stored overnight. Then the solution was allowed to warm up to 16° C. and pins having a temperature of 55° C. were immersed into the solution to prepare capsule shells. The pins were then withdrawn from the aqueous HPMCA solution and a film formed on the molding pins. The capsule shells were dried at 80° C. for 3 hours.

All films had good mechanical properties and were flexible. The capsules were cut into small pieces of 1 cm×1 cm and the films were tested in various buffers and HCl for dissolution at 37° C. under shaking.

To test the solubility of the capsule shells prepared from the HPMCA of Examples 1 and 2 in the acidic environment of the stomach, capsule pieces were immersed into 0.1 N HCl. The capsule pieces were left there for 2 hours at a temperature of 37° C. to simulate the stomach fluid. The capsule pieces prepared from the HPMCA of Examples 1 and 2 did not dissolve in 0.1 N HCl during these 2 hours.

To test the solubility of the capsule shells in the intestine or colon, capsule pieces were immersed for 2 hours into McIlvaine's buffer solutions (containing disodium monophosphate and citric acid) that had a temperature of 37° C. and a pH of 5.0; 5.5; 6.0 or 6.8, respectively. The capsule pieces prepared from the HPMCA of Examples 1 and 2 did not dissolve in the McIlvaine's buffer solution. Other capsule pieces were immersed for 2 hours into aqueous phosphate buffers of 0.2 M tribasic sodium phosphate that had a temperature of 37° C. and a pH of 5.5; 5.8; 6.0; 6.5 or 6.8, respectively. The capsule pieces prepared from the HPMCA of Examples 1 and 2 did not dissolve in the aqueous phosphate buffers either.

The invention claimed is:

1. A process for producing an aqueous composition comprising a cellulose ether acetate being at least partially dissolved in an aqueous liquid, wherein the cellulose ether acetate comprises acetyl groups as the only ester groups and the process comprises the step of
mixing an aqueous liquid with a cellulose ether acetate having a degree of substitution of acetyl groups, DSAc, of from 0.05 to 0.75 and
setting the temperature of the mixture of the cellulose ether acetate and the aqueous liquid to less than 10° C. to at least partially dissolve the cellulose ether acetate in the aqueous liquid.

2. The process of claim 1 wherein the cellulose ether acetate has a degree of substitution of methyl groups, DSM, of from 1.60 to 2.05.

3. The process of claim 1 wherein the temperature of the mixture of the cellulose ether acetate and the aqueous liquid is set to less than 5° C.

4. The process of claim 1 wherein the cellulose ether acetate has a degree of substitution of acetyl groups, DSAc, of from 0.25 to 0.70.

5. The process of claim 1 wherein after at least partial dissolution of the cellulose ether acetate in the aqueous liquid at a temperature of less than 10° C. the temperature of the aqueous composition is increased to not more than 25° C.

6. The process of claim 1 wherein the cellulose ether acetate is a hydroxypropyl methylcellulose acetate.

7. The process of claim 1 wherein the produced aqueous composition comprises at least 2.0 weight percent hydroxypropyl methylcellulose acetate dissolved in the aqueous liquid.

8. A process for manufacturing capsule shells comprising the steps of
producing, according to the process of claim 1, an aqueous composition comprising a cellulose ether acetate at least partially dissolved in an aqueous liquid, and
contacting dipping pins having a higher temperature than the aqueous composition with the aqueous composition or with the portion of the aqueous composition wherein cellulose ether acetate is dissolved.

9. A process for coating dosage forms comprising the steps of
producing, according to the process of claim 1, an aqueous composition comprising a cellulose ether acetate at least partially dissolved in an aqueous liquid, and
contacting dosage forms with the aqueous composition or with the portion of the aqueous composition wherein cellulose ether acetate is dissolved.

10. A process for preparing a solid dispersion of an active ingredient in a cellulose ether acetate comprising the steps of
producing, according to the process of claim 1, an aqueous composition comprising a cellulose ether acetate at least partially dissolved in an aqueous liquid,
dissolving an active ingredient in the aqueous composition or in the portion of the aqueous composition wherein cellulose ether acetate is dissolved, and
drying the aqueous composition or the portion of the aqueous composition wherein cellulose ether acetate and active ingredient are dissolved to produce the solid dispersion of an active ingredient in a cellulose ether acetate.

* * * * *